United States Patent [19]

Pontius

[11] Patent Number: 5,474,911
[45] Date of Patent: Dec. 12, 1995

[54] PROMOTION OF HIGH SPECIFICITY MOLECULAR ASSEMBLY

[75] Inventor: Brian W. Pontius, Palo Alto, Calif.

[73] Assignee: The Board of Trustees of Leland Stanford Jr. University, Stanford, Calif.

[21] Appl. No.: 621,424

[22] Filed: Nov. 30, 1990

Related U.S. Application Data

[63] Continuation-in-part of Ser. No. 557,227, Jul. 24, 1990, abandoned, which is a continuation-in-part of Ser. No. 444,179, Dec. 1, 1989, Pat. No. 5,015,569.

[51] Int. Cl.$^6$ .............................. C07H 21/00; C12P 1/00
[52] U.S. Cl. .............................. 435/41; 435/6; 435/68.1; 435/69.3; 435/70.1; 435/820; 436/501; 530/350; 530/358; 530/387.1; 536/22.1; 536/25.3; 935/78

[56] References Cited

U.S. PATENT DOCUMENTS

| | | | |
|---|---|---|---|
| 4,391,904 | 7/1983 | Litman et al. | 435/7 |
| 4,563,417 | 1/1986 | Albarella et al. | 435/6 |
| 4,683,195 | 7/1987 | Mullis et al. | 435/6 |
| 4,689,294 | 8/1987 | Boguslawski et al. | 435/6 |
| 4,749,647 | 6/1988 | Thomas et al. | 435/6 |
| 4,787,963 | 11/1988 | MacConnell | 204/180.1 |
| 4,833,084 | 5/1989 | Carrico | 435/240.27 |
| 5,015,569 | 5/1991 | Pontius | 435/6 |
| 5,132,207 | 7/1992 | Kohne et al. | |

FOREIGN PATENT DOCUMENTS

| | | |
|---|---|---|
| 0326100 | 8/1989 | European Pat. Off. |
| 2175906 | 12/1986 | United Kingdom |
| WO88/01302 | 2/1988 | WIPO |
| WO90/12116 | 10/1990 | WIPO |

OTHER PUBLICATIONS

Hames et al., (Ed.) *Nucleic acid hybridisation, a practical approach* (IRL Press, Oxford, England, 1985), pp. 47–71.
Hutton et al. (1973) Journal of Molecular Biology, vol. 77, pp. 495–500.
Wetmur (1971) Biopolymers, vol. 10, pp. 601–613.
Wetmur et al. (1968) Journal of Molecular Biology, vol. 31, pp. 349–370.
Myers et al. (1985) Nucleic Acids Res., vol. 13, No. 9, pp. 3111–3129.
Brown et al. (1982) Gene, vol. 20, pp. 139–144.
Pontius et al. (1990) Proc. of Natl Acad. Sci (USA), vol. 87, pp. 8403–8407.
Pontius et al. (1991) Proc. of Natl Acad Sci (USA), vol. 88, pp. 8237–8241.
Pontius, B. W., et al., "Renaturation of complementary DNA strands mediated by purified mammalian heterogeneous nuclear ribonucleoprotein A1 protein: Implications for a mechanism for rapid molecular assembly," *Proc. Natl. Acad. Sci. USA*, 87:8403–8407, (Nov., 1990).
Manfioletti, G. and Schneider, C., "A New and Fast Method for Preparing High Quality lambda DNA Suitable for Sequencing," *Nucl. Acids Res.* 16:2873–2884 (1988).
Wilchek, M. and Bayer, E. A., "The Avidin–Biotin Complex in Bioanalytical Applications," *Anal. Biochem.* 171:1–32 (1988).
Meinkoth, J. and Wahl, G., "Hybridization of Nucleic Acids Immobilized on Solid Supports," *Anal. Biochem.* 138:267–284 (1984).
Ivanov, I. G. and Markov, G. G., "RNA–DNA Hybridization on Membrane Filters with Fragmented Mammalian DNA," *Biochim. Biophys Acta* 383:123–130 (1975).
Weinstock, G. M., et al., "ATP–Dependent Renaturation of DNA Catalyzed by the recA Protein of *Escherichia coli*," *Proc. Natl. Acad. Sci. USA* 76:126–130 (1979).
Cox, M. M. and Lehman, I. R., "Renaturation of DNA: A Novel Reaction of Histones," *Nuc. Acids Res.* vol 9, No. 2, pp. 389–400 (1981).
Bryant, F. R., et al., "Kinetic Modeling of the RecA Protein Promoted Renaturation of Complenetary DNA Strands," *Biochem.* 28:1062–1069 (1989).
Kumar, A., et al., "Purification and Domain Structure of Core hnRNP Proteins A1 and A2 and Their Relationship to Single–stranded DNA-binding Proteins," *J. Biol. Chem.* vol. 261, No. 24, Issue of Aug. 25 pp. 11266–11273 (1986).
Cobianchi, F., et al., "Mammalian Heterogenous Nuclear Ribonucleoprotein Complex Protein A1," *J. Biol. Chem.* vol. 263, No. 2, Issue of Jan. 15, pp. 1063–1071 (1988).
Merrill, B. M., et al., "Phenylalanines that are Conserved among Several RNA-binding Proteins Form Part of a Nucleic Acid-binding Pocket in the A1 Heterogeneous Nuclear Ribonucleoprotein," *J. Biol. Chem.* vol. 263, No. 7, Issue of Mar. 5, pp. 3307–3313 (1988).
Keener, S. L. and McEntee, K., "Homologous Pairing of Single-stranded Circular DNAs Catalyzed by recA Protein," *Nucl. Acids Res.* vol. 12, No. 15, pp. 6127–6139 (1984).
Christiansen, C. and Baldwin, R. L., "Catalysis of DNA Reassociation by the *Escherichia coli* DNA Binding Protein," *J. Mol. Biol.* 115:441–454 (1977).
Dreyfuss, G., et al., "Heterogeneous nuclear ribonucleoprotein particles and the pathway of mRNA formation," *TIBS*, 13:86–91 (Mar. 1988).
Bandziulis, R. J., et al., "RNA–binding proteins as developmental regulators," *Genes & Development*, 3:431–437 (1989).
Williams, K. R., et al., "Amino acid sequence of the UP1 calf thymus helix–destabilizing protein and its homology to an analogous protein from mouse myeloma," *Proc. Natl. Acad. Sci. USA*, vol. 82, pp. 5666–5670, (Sep. 1985).
Cobianchi, F. et al., "Structure of Rodent Helix–destabilizing Protein Revealed by cDNA Cloning," *The Journal of Biological Chemistry*, vol. 261, No. 8, Issue of March 15, pp. 3536–3543, (1986).

*Primary Examiner*—W. Gary Jones
*Assistant Examiner*—Ardin H. Marschel
*Attorney, Agent, or Firm*—Townsend and Townsend and Crew

[57] ABSTRACT

This invention relates to an improvement in promoting the rate of association for high specificity binding pairs used in a variety of industrial, research and medical applications. These pairs include enzyme/substrate, complementary polynucleotide and antibody/antigen combinations. In one specific embodiment, this invention relates to the acceleration of nucleic acid hybridization by heterogeneous nuclear ribonucleoproteins [hnRNPs]. In another specific embodiment, this invention relates to the acceleration of nucleic acid hybridization by a cationic detergent.

20 Claims, No Drawings

PROMOTION OF HIGH SPECIFICITY MOLECULAR ASSEMBLY

The U.S. Government has a paid-up license in this invention and the right in limited circumstances to require the patent owner to license others on reasonable terms as provided for by the terms of Grant No. GM 13235 awarded by the National Institutes of Health. This application is a continuation-in-part application of U.S. Ser. No. 07/557,227, filed Jul. 24, 1990 (now abandoned), which is a continuation-in-part application of U.S. Ser. No. 07/444,179, filed on Dec. 1, 1989, now issued as U.S. Pat. No. 5,051,569.

BACKGROUND OF THE INVENTION

1. Field of the Invention

This invention relates to an improvement in promoting the rate of association for high specificity binding pairs used in a variety of industrial, research and medical applications. These pairs include enzyme/substrate, complementary polynucleotide and antibody/antigen combinations. In one specific embodiment, this invention relates to the acceleration of nucleic acid hybridization by heterogeneous nuclear ribonucleoproteins [hnRNPs]. In another specific embodiment, this invention relates to the acceleration of nucleic acid hybridization by a cationic detergent.

2. Information Disclosure

The acceleration of annealing between complementary nucleic acids has been described. Christiansen C. and Baldwin, R. L., 1977, Catalysis of DNA Reassociation by the *Escherichia coli* DNA Binding Protein, J. Mol. Biol. 115:441–454; Weinstock, G. M. et al., 1979, ATP-dependent renaturation of DNA catalyzed by the recA protein of *Escherichia coli*, Proc. Natl. Acad. Sci. 76:126–130; Cox, M. M. and Lehman, I. R., 1981, Renaturation of DNA: a novel reaction of histones, Nucleic Acid research 9:389–399; Keener S. L. and McEntree, K., 1984, Homologous pairing of single-stranded circular DNAs catalyzed by recA protein, Nucleic Acids Research 12:6127–6139; and Bryant, F. R. et al., 1989, Kinetic Modeling of the RecA Protein Promoted Renaturation of Complementary DNA Strands, Biochemistry 28:1062–1069.

Heterogeneous nuclear particles was known and reviewed by Dreyfuss, G., et al., March 1988, Heterogeneous nuclear ribonucleoprotein particles and the pathway of mRNA formation, TIBS 13:86–90 and Bandziulis, R. J. et al., 1989, RNA-binding proteins as developmental regulators, Genes & Devel. 3:431–437.

The A1 core protein has been implicated in helix-destabilization. Williams, K. R. et al., 1985, Amino acid sequence of the UP1 calf thymus helix-destabilizing protein and its homology to an analogous protein from mouse myeloma, Proc. Natl. Acad. Sci. USA 82:5666–5670. The cDNA encoding A1 hnRNP from rat has been cloned and expressed. Cobianchi, F. et al., 1986, Structure of Rodent Helix-destabilizing Protein Revealed by cDNA Cloning, J of Biol. Chem. 261:3536–3543. The A1 hnRNP from human cells has been isolated and purified. Kumar, A. et al., 1986, Purification and Domain Structure of Core hnRNP Proteins A1 and A2 and Their Relationship to Single-stranded DNA-Binding Proteins, J. Biol. Chem. 261:11266–11273. Kumar et al also reported on the ability of A1 hnRNP to mediate duplex formation between synthetic polynucleotides.

The characterization of mammalian A1 hnRNP was described by Cobianchi, F. et al. 1988, Mammalian Heterogeneous Nuclear Ribonucleoprotein Complex Protein A1, J. Biol. Chem. 263:1063–1071 and by Merrill B. M. et al., 1988, Phenylalanines That Are Conserved among Several RNA-binding Proteins Form Part of A Nucleic Acid-binding Pocket in the A1 Heterogeneous Nuclear Ribonucleoprotein, J. Biol. Chem. 263:3307–3313.

SUMMARY OF THE INVENTION

This invention relates to a method for accelerating the association rate constant for members of primary binding pairs in the absence of aggregate formation by the primary binding pairs, said method comprising (a) attaching complementary members of secondary binding pairs to the members of primary pairs where the secondary binding pairs have a $k_a$ larger than the $k_a$ of the primary binding pairs; and (b) placing the members in a solution under conditions which permit binding between members of the primary binding pair. The increase in the association rate is preferably at least about 10 times and more preferably at least about 100 times. The preferred primary binding pairs are selected from the group consisting of complementary polynucleotides; antibody and corresponding antigen; and, enzyme and its substrate. The secondary binding pairs are preferably selected from the group consisting of: hydrophobic polymers such as long chain alkyl groups or polypeptides containing hydrophobic residues, acidic and basic polymers containing multiple glutamic or aspartic acid and lysine or arginine residues, and acidic and basic polymers such as nucleic acids and nucleic acid binding proteins containing repeating units. The complementary secondary binding pair members can be bound to the primary binding pair members through a covalent or noncovalent (e.g., ionic or hydrophobic bonds) interaction.

In a preferred embodiment, the complementary secondary binding pair consists of oppositely charged polymers, and the primary binding pair consists of an antibody and corresponding antigen. In another preferred embodiment, the complementary secondary binding pairs are heterogeneous ribonucleoproteins and the DNA backbone and the primary binding pairs are complementary polynucleotides. In another preferred embodiment, the primary binding pairs are complementary nucleic acid and the secondary binding partner is a cationic detergent attached noncovalently to the nucleic acid backbone. In yet another preferred embodiment, the complementary secondary binding pairs are comprised of polypeptide segments having multiple positively charged groups and polypeptide segments having negatively charged groups. These polypeptide segments may comprise multiple arginine, lysine, glutamic acid or aspartic acid residues. The polypeptide segments are typically between about 100 to about 500 angstroms long and more typically about 10 to about 100 angstroms in length.

This invention further comprises compositions consisting of a member of a primary binding pair covalently bound to a member of a secondary binding pair where the members of the second pair exert a force of attraction for each other which exceeds the force that the primary binding pair members attract upon each other at a distance which permits more than one member to compete for a single binding site on a complementary member of primary binding pair. In an analogous embodiment, the composition comprises a first primary binding pair member covalently bound to a secondary binding pair member which functions to attract a second and complementary primary binding pair member unmodified by a distinct secondary binding pair member. This attraction can be via a natural or preexisting high probability binding site or domain on that primary binding pair member. Alternatively, the primary binding pair member may comprise a domain of a single charge or moiety which can exert a mutual attraction between itself and the secondary binding pair member covalently bound to the first primary binding pair member. This avoids having to modify both primary binding members. It is preferred that the secondary binding pair members or members sites have association rate constant which exceeds the association rate constant of the primary binding pairs. A preferred embodiment encompasses secondary binding pairs which comprise polypeptide segments having multiple positively charged groups and polypeptide segments having multiple negatively charged groups. Preferred primary binding pairs include antibodies and their corresponding antigens, enzymes and their substrates, and complementary polynucleotides.

This invention further provides methods for accelerating the association rate constant for members of a primary binding pair binding in the absence of aggregate formation by the primary binding pairs said method comprising (a) contacting an aqueous solution containing the members with a multivalent association rate enhancer having the ability to physically bind to each other and/or to more than one of the members of the binding pairs; and, (b) incubating the binding pairs under conditions which permit association of the binding pairs and the multivalent rate enhancers. A preferred embodiment encompasses complementary polynucleotides as primary binding pairs and either A1 hnRNP or polylysine as the multivalent rate enhancers.

In a more specific embodiment, this invention provides for a method for accelerating the rate of hybridization between two complementary nucleic acid sequences in an in vitro nucleic acid hybridization assay comprising: (a) hybridizing two complementary nucleic acid sequences in a hybridization reaction mixture under conditions permitting nucleic acid hybridization where the reaction mixture comprises heterogeneous nuclear ribonucleoprotein having a carboxy terminus capable of nucleic acid:hnRNP/nucleic acid:hnRNP interaction, said ribonucleoprotein present in an amount sufficient to substantially accelerate the rate of hybridization above the hybridization rate in the absence of the ribonucleoprotein; and (b) detecting the hybridization of the two complementary nucleic acid sequences. In a second embodiment, there is an optional proviso that neither of the nucleic acid sequences being detected is a polyribouridylic acid. In a preferred embodiment, the ribonucleoprotein may be A1 core protein or UP1. Mammalian ribonucleoproteins, such as rat, are preferred. It is preferred that the ribonucleoprotein's carboxy tail be glycine rich. The amount of heterogeneous ribonucleoprotein should be at least about a 5 fold excess by weight of the total amount of nucleic acid in the reaction mixture. The nucleic acids are preferably longer than 25 bases and can be either DNA or RNA.

In yet another embodiment, this invention provides for a method for accelerating the association rate constant for members of a primary binding pair in an enzyme reaction said method comprising (a) by attaching a polymer to the enzyme, said polymer binding with high probability to the substrate such that the polymer and substrate have a $k_a$ larger than the $k_a$ of the enzyme and substrate; and (b) placing the members in an aqueous solution under conditions which permit binding between members of the primary binding pair. In a preferred embodiment, the polymer contains multiple positively charged groups, such as multiple lysine residues, and the enzyme is a nuclease and the substrate is a polynucleotide. The preferred nucleases include restriction endonucleases and ribozymes.

In another embodiment, this invention provides for a method for conducting a high temperature nucleic acid hybridization assay having a target nucleic acid and a probe nucleic acid comprising: (a) hybridizing two complementary nucleic acid sequences in a hybridization reaction mixture under conditions permitting nucleic acid hybridization, including temperatures at about 45° C. or above, where the reaction mixture comprises single stranded nucleic acid binding compounds present in an amount sufficient to substantially accelerate the rate of hybridization above the hybridization rate in the absence of the compound and where the numbers of probe nucleic acid to target nucleic acid does not approximate a 1 to 1 ratio; and (b) detecting the hybridization of the two complementary nucleic acid sequences. In a preferred embodiment, the compound is a heterogeneous ribonucleoprotein, the high temperature is preferably about 65° C., and the nucleic acid is DNA.

This invention also provides for kits encompassing multiple compartments for the various reagents needed to use the invention as described herein. These include kits having compartments with primary binding pairs such as nucleic acids or antibodies, compartments with hybridization reagents, and compartments with secondary binding pairs such as heterogeneous nuclear ribonucleoproteins having a glycine-rich carboxy terminus. Where the kit further comprises nucleic acids as primary binding pairs, the nucleic acids can be labelled with a reporter such as an enzyme or a fluorophore.

DEFINITIONS

"A force of attraction for each other which exceeds the force that the primary binding pair members attract upon each other at a distance which permits more than one member to compete for a single binding site on a complementary member of primary binding pair" functionally describes the minimum amount of attraction necessary to use the claimed method. The actual force is typically determined empirically by the methods described herein.

"A1 core protein" refers to a protein of approximately 34 kD which is found associated with hnRNA in the nucleus of eucaryotic cells and which is composed of two consensus nucleic acid binding domains and a glycine-rich carboxy terminus.

"Aggregate formation" refers to a reaction where primary binding pairs are binding into a stable complex of members, in substantial excess of two. Typically this reaction is detected by the presence of insoluble particles which either precipitate out spontaneously or are removable by filtration or centrifugation.

"Antibody and corresponding antigen" refers to an antibody and the antigen to which it binds.

"Association rate constant" refers to the rate at which complementary members of a binding pair form a complex. It is measured in liters of complex formation per mole per second. For the case where two molecules are coming together to form a complex, (e.g., A+B ←→AB), the rate of formation is equal to $k_a$[A][B]. [A] is the concentration of A in solution, [B] is the concentration of B in solution, and $k_a$ is the association rate constant. Lower rates of association exist where there is little mutual attraction over significant distances and where complex formation averages multiple random collisions between members before complex formation occurs. Binding members having low $k_a$ rely on Van der Waal forces or hydrogen bond formation to provide the energy of complex formation. High rates of association exist where the members mutually attract each other to bring about a greater number of contacts which increase the opportunity for complex formation. Such binding members rely on electrostatic and hydrophobic interactions.

"Carboxy terminus" refers to that half of a polypeptide bearing the free α-carboxy group.

"Cationic detergent" refers to a detergent having a positively charged group and a hydrophobic domain. Examples include cetylpyridinium chloride, dodecyltrimethylammonium chloride, hexadecyltrimethylammonium chloride and tetradecyltrimethylammonium bromide.

"Complementary members" refers to any two molecules which can bind to each other and unless otherwise limited encompasses both high and low specificity binding pairs and high and low probability binding pairs.

"Covalently bound" refers to a bond between two atoms where a pair of electrons are shared.

"DNA backbone" refers to the phosphate groups which typically impart an overall negative charge to a nucleic acid.

"Nuclease" refers to an enzyme which cleaves the phosphodiester bonds of nucleic acid. This term embraces ribozymes and restriction endonucleases.

"Glycine rich" refers to polypeptides or regions of polypeptides which comprise about 20 to 80% glycine residues.

"Hydrophobic polymers" are those polymers which comprise units that are less polar than water and tend to associate with other hydrophobic polymers in an aqueous environment.

"In an amount sufficient to substantially accelerate" is a quantity which is empirically determined by the methods described herein and where "substantially accelerate" refers to a statistically meaningful increase.

"Multivalent association rate enhancer" refers to a macromolecule such as A1 hnRNP which has multiple sites with which it may either bind with high probability to other multivalent association rate enhancers and/or to the primary binding partners. These macromolecules also enhance or increase association rates for primary binding partners as described herein.

"Negatively or positively charged groups" refers to moieties on a polymer such as carboxyl, phosphate, or amine groups.

"Nucleic acid sequences" refers to nucleic acids in a polymeric form. Typically this is the naturally occurring 5'–3' ribose phosphate backbone. Both natural and synthetic polymers are operable in this invention. Such synthetic polymers would include unnatural bases and variations in the natural 5' to 3' bonding. The size of the sequence is not critical. Typically the polymers are of a size to permit hybridization to be sufficiently specific to function successfully in the assay and avoid nonspecific binding to nontargets. Preferably the polymers are from about 25 nucleotides long up to several kilobases. Exact complementarity between strands is not required. By varying the stringency of the hybridization mixture, one can achieve satisfactory results with strands of nucleic acid that are not exact complements of each other.

"Polymers" when described as either acidic or basic encompass molecules of repeating units which are either uniform or at least about 10% units which bear at least one proton releasing (acidic) or protein accepting group (basic). Examples include polyglutamic acids and polylysine.

"Polymer binding with high probability to the substrate" refers to a polymer with a repeating structure, each unit of which can bind independently to the substrate with low affinity, using electrostatic interactions and/or hydrophobic interactions.

"Polypeptide segments" refers to amino acid chains linked by peptide bonds.

"Primary binding pairs" refers to a ligand/receptor combination in which the members interact in a highly specific manner without significant mutual long distance forces of attraction so that at concentrations where members are at an average distance apart where multiple members can compete for a given opposite member, random motion dominates the probability that any one member will bind to a particular complementary member.

"Protein members" refers to binding pair partners which comprise at least 70% amino acid residues.

"Oppositely charged polymers" refers to polymers which are capable of attracting each other through positive and negative ionic forces.

"Reporter" refers to substituents or moieties that are detectable and act as signals or labels in binding assays to permit the presence or absence of the entity to be assayed. These include enzyme labels, radioactive labels and fluorescent labels.

"Residues" when referring to an amino acid, e.g., lysine, encompasses the specified amino acid although a part of the peptide chain.

"Secondary binding pairs" refers to a ligand/receptor combination in which the members interact in a relatively nonspecific manner and where the members exert a significant long distance mutual attraction upon each other.

"Single-stranded nucleic acid binding compounds" refers to substances which associate with nucleic acid of any sequence and are able to function as secondary binding pair members. These include cationic detergents and single stranded nucleic acid binding proteins (hnRNP).

"Solid support" refers to an insoluble entity to which binding members can be attached in a manner in which they can still bind to their complementary partners.

DETAILED DESCRIPTION

This invention provides for a valuable means for increasing the association rate constant for two members of a high specificity binding pair (primary binding pair). Means to increase the rate of association between binding pairs is of great importance to industry, medicine and research.

The purpose of this invention is to increase the rate of association for highly specific biological binding partners. The primary binding partners are ligand/receptor pairs which do not exert a strong mutual attraction for each other over distances which exceed their combined radius. Initial interactions between primary binding partners are primarily due to random movement within the medium (typically a buffered aqueous solution). Once two primary binding partners are in sufficiently close proximity to engage strong intermolecular attraction, binding is assured. Examples of primary binding pairs are DNA/DNA complementary binding pairs, enzyme/substrate binding pairs, antibody/antigen binding pairs and hormone/receptor binding pairs.

Examples of procedures where relying upon interactions between high specificity binding pairs is required include: (a) nucleic acid hybridization assays such as southern and northern assays, subtraction hybridization, polymerase chain reaction assays, ligase amplification assays, ligation mediated detection assays and RNAase protection assays; (b)

antibody: antigen complex formation for ELIZA assays, radioimmunoassays, immunoprecipitations, western blots, and cancer chemotherapy; and, (c) enzyme mediated catalysis such as nucleolytic attack, proteolysis, and catalysis of small molecule conversion.

The interaction of molecules in solution is limited by the rate with which the interacting components diffuse to within a distance sufficient for a binding interaction to occur. This distance is a function of the size and the nature of the binding site through which the molecules interact.

The binding sites of most macromolecules are highly specific for their ligand. They take advantage of various physical forces, including electrostatic forces, hydrogen bonds, Van der Waals forces, and hydrophobic interactions.

I. ASSOCIATION RATE CONSTANTS

The association rate constant for binding of molecules can vary, depending on the types of interactions involved and the rate of diffusion of the interacting components. High specificity interactions generally take advantage of all forces. However, electrostatic forces and hydrophobic interactions will act over longer distances in solution and are often responsible for the initial attraction between members leading to a specific binding interaction which results from the increase in affinity as distance between binding pairs decreases. Complex formation of binding pairs results from the formation of specific contacts mediated through all physical forces (e.g., hydrogen bonding, electrostatic, hydrophobic and Van der Waals forces). This two phase process can be outlined as:

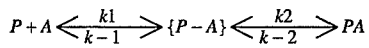

Only the rate of formation of the encounter complex is dependent upon the concentration of reactants, P and A, in solution. For most interactions, the reaction is limited by the rate with which components encounter each other in solution, which is $k1(P)(A)$. If $k2$ is fast with respect to $k1$, and greater than the initial dissociation constant, $k-1$, the rate with which complex formation takes place will be determined by the rate of diffusion, which is taken as:

$$k_D = 4 \, pi \, N_A(D_P + D_A)r_{PA}$$

$N_A$ = Avogadro's Number $D_P$, $D_A$ = Diffusion Coefficients

The distance at which the molecules interact, $r_{PA}$, is a function of the binding interaction which takes place at the greatest distance in solution, and can lead to the formation of the high affinity complex. The $k_D$ for the association of two large molecules (proteins, DNA) in solution are typically $10^8/\underline{M}/s$. For the interaction of a large and a small molecule (enzymes:substrates), the rates are $10^9/\underline{M}/s$. If the initial interaction between components does not include forces which act at a distance (e.g., complementary electrostatic interactions or hydrophobic forces), and instead, relies on forces which are mediated over short distances (e.g., hydrogen bonds or Van der Waals forces), the rpA and therefore the $k_D$ of the association will be considerably less. Increasing the distance at which these molecules can interact can be expected to give a corresponding increase in the rate of association, provided that the interaction at a distance can lead to the more specific association. *Proteins* by Thomas E. Creighton (1983) W. H. Freeman and Co. Chapters 4,8 offers a good conceptual review of association rate constants.

Because this invention involves increasing association rate constants for a variety of binding pairs, measurement of such rate constants is helpful to optimize assay conditions. Association rate constants can be calculated in a variety of accepted and well-known ways:

1) Nucleic Acid Hybridization

Under conditions where little strand melting occurs (i.e., below the melting temperature of the nucleic acid) the rate of annealing can be calculated by measuring the amount of loss of single stranded substrate at various times, or by measuring the amount of formation of double stranded product. The amount of single strands can be measured by S1 nuclease sensitivity assays. The amount of double stranded material can be measured by hydroxyapatite binding. Optical hyperchromicity can also be used. Alternatively, single strands can be separated from double strands by gel electrophoresis by virtue of their different mobilities. For DNA molecules with defined ends, the association rate constant for annealing can be derived from the equation:

$$H = (1 + k_a \, C_o \, t)^{-1}$$

Where:  $H$ = fraction of single strands remaining
$k_a$ = association rate constant
$C_o$ = original concentration of nucleotides
$t$ = time of incubation in seconds
(Nucleic Acid Hybridization Ed. Hames B.D., Higgins S.J. IRL Press (1985)

2) Antibody:Antigen Interactions

Antibody:antigen interactions generally have association rate constants of $10^8 \underline{M}^{-1} \, s^{-1}$. These have been calculated by absorption spectroscopy, Using methods such as relaxation or stopped flow. Equilibrium association constants for antibody:antigen interactions can vary from less than $10^4$ for weak association, to greater than $10^8 \, M^{-1}$ (*CRC Critical Rev. Immunology* (1986) 6: (1)p1–46)

3) Enzyme:Substrate Interactions

For reactions where the enzyme is not saturated with substrate (where an addition of substrate leads to a more rapid rate of product formation), an increase in the rate of association of enzyme with substrate would be expected to lead to increased product formation. Enzyme:substrate interactions are generally rapid, with association rate constants between $10^7$–$10^9$. Because of this, sophisticated methods of obtaining data to calculate rate constants are used. These include:

(a) Rapid Mixing Techniques Using
  A Continuous flow apparatus
  Stopped-flow spectrophotometry
  Rapid quenching to stop the reaction (b) Flash Photolysis to generate substrate in a premixed solution (c) Relaxation methods, such as
  Temperature jump experiments (*Enzyme Structure and Mechanism* Alan Fersht, W. H. Freeman (1985)

This invention takes advantage of a specific class of binding pairs termed high probability binding sites. These binding members utilize electrostatic and hydrophobic interactions to provide a greater force of attraction between binding pairs at a distance. When such molecules are attached either directly or indirectly to members of a binding pair having a high specificity for each other, there is a significant increase in the association rate constant for the high specificity binding interaction.

II. SECONDARY BINDING PAIRS

With the above explanation of complex formation between binding pairs, the following definition is offered as a guide for the selection of those binding pairs (secondary binding pairs) which will function to increase the apparent association rate constant of the high specificity binding pairs or primary binding pairs. For purposes of this discussion, the secondary binding pairs preferably are members which interact with their complementary member over a relatively great distance through electrostatic or hydrophobic interactions with complex formation being relatively nonspecific and occurring with a high degree of probability upon initial contact.

The properties which identify the secondary binding pairs, with their high probability binding sites, include binding sites which are relatively homogeneous with respect to the type of interacting chemical group such that any part of one binding site can react with any part of the corresponding binding site. An example of binding partners with homogeneous binding sites would be a binding member comprised of a polymer having multiple positive charges and a complementary partner that is comprised of multiple negative charges. Another possibility would be to have both secondary binding pair members be hydrophobic. Hydrophobic binding partners can be composed of multiple hydrophobic amino acid residues, such as leucine or isoleucine. They can be interspersed with amino acids which destabilize secondary structure to promote an extended, flexible configuration. One could also construct a repeating unit which would incorporate both electrostatic and hydrophobic constituents. In this way, complex formation is relatively nonspecific and arises when any part of one binding pair contacts any part of its complementary binding pair.

The binding of the secondary binding pair functions to spatially orient the members of the primary binding pair in close proximity to each other. This increases the probability, and therefore the rate of binding events between the primary binding pairs which typically exert less mutual attraction on each other than the secondary binding pair at relatively large distances. By "relatively large distances", it is meant that the distance is such that primary binding is not assured, and could still be disrupted by random thermal motion. In other words, it is meant that the distance is of a sufficiently large radius that more than one member can compete for a particular binding site on a corresponding partner. As primary binding sites get increasingly close, the binding forces which attract them together can become greater than the binding force of the secondary binding interaction. This would generally occur on the order of a few angstroms. The secondary binding pairs are designed such that they can interact even when the primary binding sites are tens of angstroms apart.

The binding sites on the members of the secondary binding pairs should be physically large. A relatively large site will increase the probability of a binding event between the secondary binding pairs. Enlarging the size of a binding site would involve the addition of more repeating units to the binding site. An example of enlarging the binding site would be to increase the length of secondary binding pairs comprising polylysine and polyglutamate from tripeptides to decapeptides. It should be noted that the size of the secondary binding sites could be optimized so as to maximize the rate of formation of the primary binding interaction once the secondary binding interaction has occurred. The size should not permit the primary binding pair to separate beyond the average distance which exists between noninteracting primary binding pairs in solution, when the secondary binding pairs are interacting with each other.

The secondary binding members are preferably composed of flexible tails. Flexible structures offer several advantages. These tails allow corresponding binding sites to interact from any orientation in solution. If a binding site was on one face of a globular protein, only that face would be a potential binding partner. In addition, flexible secondary binding pairs allow for orientations and associations of the high specificity binding members, through brownian motion, without requiring dissociation of the secondary binding pairs. Flexible tails could be ensured by incorporating chemical constituents which are themselves flexible, or which are unlikely to fold into a globular structure. Secondary binding members with this property include polypeptides incorporating glycine and proline residues, long alkyl chains (of about 5 to about 20 carbons), and synthetic polymers such as dextran sulfate.

The secondary binding pairs should have a mutual attraction which operates over the longest possible distance and in any orientation. This could be achieved by using charge:charge interactions or hydrophobic constituents. Charge:charge interaction involve moieties having positive charges such as mono or polyprotic bases (e.g., amino groups or metal ions) and negatively charged moieties such as mono or polyprotic acids. The charged region can be uniformly composed of charged amino acids or have such amino acids randomly inserted so that the interacting domains are capable of binding to each other. Hydrophobic interaction is illustrated by long alkyl chains. While these types of interactions inherently provide a mutual attraction over a relatively long range, incorporating them into a long, flexible tail would provide for an even greater increase in their ability to mutually attract over distances. Amino acids which are charged or which have hydrophobic character are well known.

The use of multiple high probability binding members attached to each member of the primary binding pair can facilitate the complex formation between members of the primary binding pair. This would increase the likelihood of a binding partner undergoing a high specificity binding event. For example, for processes such as nucleic acid annealing, multiple high probability binding partners such as multiple A1 hnRNP proteins attached along the DNA molecule might allow multiple high probability interaction events, thereby increasing the likelihood of a productive nucleation event. In this case, the length of the individual secondary binding pairs can be shortened, as the effect of having multiple secondary binding pairs on a polymer, which is itself flexible, allows the entire molecule to act as a secondary binding partner.

Using the methods described below, one can design the specific placement of the high probability binding site so as to increase the proximity of the high affinity binding sites of the primary binding pair once the high probability reaction takes place. For example, the high probability binding site could be attached near the active site of an enzyme so as to channel the substrate to the active site.

It would also be preferred to attach several small high probability binding partners along the backbone of a nucleic acid strand, rather than have one large high probability binding partner at the end of a strand, as this configuration would be more likely to cause an alignment of the strands after initial association had occurred, thereby further increasing the proximity of nucleotides on opposite strands, and thereby increasing the rate of specific association. It is preferable that initial binding of the primary binding pair can be achieved without complete dissociation of the secondary binding pair members.

Under certain conditions, high probability interactions can occur between secondary binding pairs without high specificity binding potential. An example of this is when non-complementary A1 hnRNP coated nucleic acid strands interact with each other in solution. If noncomplementary strands associate too stably with each other, they will be prevented from associating with their complementary partners. Thus, it is important to use secondary binding pairs which do not interact with each other to form a complex which is excessively stable. It is better to have secondary binding members interact with each other with high probability, but relatively low stability.

Two general approaches are particularly useful to lower the stability of these secondary binding partner interactions. One is to change the chemical nature of the secondary binding partners, and the other is to change the aqueous environment. For example, the size of the secondary binding members could be reduced, which would lower the stability of these interactions. This would not be preferred, as it would also lower the probability of a binding event. A better method would be to introduce chemical constituents which destabilize the interaction. This could be done, for example, by replacing charged groups with neutral groups. A secondary binding member composed of polylysine could have some of the lysine residues replaced with glycine or proline. In addition, when reactions are carried out in vitro, buffer conditions could be altered so as to increase or decrease the strength of the high probability binding reaction. Increased ionic strength would lower the stability of interactions between secondary binding partners composed of charged residues. Changes in the temperature could also influence the nature of the reaction. High probability interactions should be such that the likelihood of a high specificity binding interaction is great once a high probability interaction has occurred, but sufficiently transient such that, in the absence of high specificity binding potential, dissociation takes place. Because most secondary binding members don't require a specific, stable structure in order to function, high temperatures generally do not inhibit their ability to promote rapid association. Maximal rates are likely to be achieved at temperatures just below the temperature where the primary binding interaction becomes unstable.

For example, when accelerating nucleic acid hybridizations using cationic detergents such as an alkyltrimethyl ammonium bromide, those of skill would recognize that low temperatures of approximately zero degrees celsius can cause aggregation. (Manfioletti, G. et al., 1988, *Nucl. Acids Res.* 16:2873–2884). Nonspecific aggregation is not desired and can be avoided by the use of increased incubation temperatures, preferably 60°–90° C.

The following are examples of secondary binding pairs which have high probability binding sites:

(a) Negatively charged: dextran sulphate, polyphosphate, polyglutamic acid and polyaspartic acid;

(b) Positively charged: polylysine, polyarginine and polyethylenimine;

(c) Hydrophobic, polyphenylalanine and polytryptophan and polyalkanes.

High probability binding sites can be chemically synthesized and attached to the appropriate macromolecules. Alternatively, polypeptide coding sequence, either naturally occurring or designed using the properties listed above, could be incorporated into a gene whose product contains a high specificity binding site. In addition, high probability binding sites could be attached non-covalently to the high specificity binding partners.

This invention can be performed in three different embodiments. The first embodiment utilizes a secondary binding pair which comprises two different members. These two members exert a mutual attraction upon each other and are illustrated by a polyglutamate and polylysine members. The second embodiment utilizes two identical members which mutually attract each other. Polymers which are hydrophobic such as long chain hydrocarbons (e.g., pentane, octane, etc.) will mutually attract each other in a manner similar to micelle body formation. The third embodiment uses a single multivalent macromolecule capable of high probability binding attached to one of the primary binding partners to increase the apparent association rate constant. The attachment can be through a covalent bond. Charged polypeptides, when covalently bound to nucleic acid, illustrates this third embodiment. The third embodiment is also illustrated by primary binding partners comprised of an antibody and an antigen, where the antigen is a virus particle, and the antibody has attached to it a secondary binding partner with high probability binding affinity to the repeating structure of the virus coat.

The members of the primary and secondary binding pairs may be covalently or noncovalently bound to each other. Where covalent, the bonding may be direct or through a linking agent. Direct linking is done via available groups which react with each other such as peptide linkages between amine/carboxyl groups, Schiff's base formation between aldehydes and amines, esterification between alcohol groups and acids and disulfide bond formation as between cysteine residues. Linking reagents are either homobifunctional or heterobifunctional compounds such as glutaraldehyde, N-hydroxy succinimidyl (NHS) esters or α-bromoacetamide. These reagents are commercially available from a variety of sources. There use is well known. See for example U.S. Pat. Nos. 4,152,411 and 4,687,732 which are incorporated herein by reference. These two patents illustrate means for covalently binding members of primary binding pairs to labels. The general teachings and methods are applicable to the covalent linking of members of a primary binding pair to members of a secondary binding pair.

If the primary and secondary binding members are bound through noncovalent means, the strength of their bond must be sufficient to ensure that at least one secondary binding member is bound to a primary binding member at most times.

III. APPLICATIONS OF SECONDARY BINDING PAIRS FOR INCREASING THE ASSOCIATION RATE CONSTANT FOR PRIMARY BINDING PAIRS

The use of secondary binding pairs has wide use in processes where the kinetics of chemical reactions involving binding of separate molecules in solution is rate limiting. These include binding reactions, such as nucleic acid annealing, as well as increasing the rates of chemical reactions. This invention has in vivo and in vitro applications. The following is a short list for the purpose of illustration only. Any reaction which is limited by the bringing together of components might be facilitated by this invention.

1) Nucleic Acid Annealing.

Nucleic acid annealing is limited by the rate of nucleation events occurring in solution. When secondary binding members with high probability binding sites are attached to nucleic acid strands, such that the binding site on one strand has a complementary partner on the complementary strand, an increased rate of association of the complementary nucleic acid strands in solution is achieved. If this association is such that the probability of a correct nucleation event is increased, the kinetics of annealing will be increased. A1 hnkNP protein, in part, facilitates annealing in this way. It is important that the complementary strands are able to move with respect to each other once high probability binding takes place so as to allow the possible association of many different pairs of bases on complementary strands so that the likelihood of a correct association is increased. In the absence of stable, high affinity base pairing, the complex dissociates.

A second example of nucleic acid annealing would be to attach a positively charged high probability binding site directly to a probe nucleic acid. This would cause a rapid, but flexible, association of the probe with target nucleic acid, thereby increasing the rate of specific association.

2) Antibody:Antigen Interactions

The attachment of a high probability binding site to an antibody and a complementary high probability binding site to its corresponding antigen would promote the specific antibody:antigen binding event. Additionally, the attachment of a high probability binding site to one antibody could be used to increase the rate of association of a second antibody with a complementary high probability binding site, to a different epitope of the same antigen. One antibody could be present in high concentration, while the second antibody could be present in low concentration. This second antibody, which could be labeled or carry a toxic compound, would then bind rapidly to any antigen to which the first antibody has already been attached. The antigen could be a protein with two different epitopes, one for each antibody. Alternatively, the antigen could be a cell which has on its surface two different proteins, each with an epitope for one of the antibodies.

When the antigen itself is composed of a repeating unit, a high probability binding partner can be attached solely to the interacting antibody molecule. The high probability binding partner would interact with the antigen with high probability, but low specificity, and thereby increase the rate with which the high specificity antibody molecule associates with the antigen. The antigen could be a virus particle with multiple identical coat proteins on its surface, or a polymeric protein such as actin. The high probability binding partner could be a small, repeating unit of a naturally occurring binding site for the antigen, or it could be a synthetic high probability binding partner. For the case of the AIDS virus (HIV), the high probability binding partner could be composed of a repeating unit of the amino acid sequence [Phe, Leu, Thr, Lys, Gly, Pro] which has been implicated in the binding of HIV to the CD4 receptor (Peterson, A. and Seed, B. (1988) Cell 54, 65–72). The high specificity binding partner could be an antibody, or other equivalent receptor molecule with high specificity binding potential. In the case of HIV, the high specificity binding partner could be the cellular receptor CD4, or a soluble variant thereof.

3) Nucleic Acid Modifying Enzymes

A secondary binding member having high probability binding sites is attached to an enzyme which modifies nucleic acid, such as a restriction enzyme, nuclease, polymerase, or other DNA modifying enzyme. The high probability binding site increases the frequency with which the nucleic acid modifying enzyme interacts with the nucleic acid thereby increasing its efficiency. A positively charged, high probability binding tail, such as polylysine or polyarginine, would be expected to interact with the negatively charged backbone of DNA. A similar tail could be used for enzymes which modify RNA. This embodiment eliminates the need for attaching a corresponding high probability binding site on the nucleic acid substrate. The nucleic acid phosphate backbone is a natural high probability binding site.

4) Proteases

A high probability binding partner which could interact with common chemical constituents on proteins could be used to increase the rate of association of a protease to its substrate. Alternatively, the high probability binding partner could be hydrophobic, so as to interact with a detergent denatured protein. If said detergent were charged, the high probability tail could also carry complementary charge to increase the kinetics of the interaction. In this way, the protease would associate with high concentrations of detergent, such as that found on a denatured protein. It may be important in this case to design a high probability binding partner which is not itself a polypeptide chain to avoid autolysis.

5) Enzyme:Smaller Substrate Interactions

A secondary binding member having high probability binding sites could be attached to an enzyme such that it bound substrate in a manner similar to the trapping of cations by DNA. The charged substrate would then diffuse along the high probability binding tail and encounter the active site of the enzyme. This would be feasible for charged substrates, and may also be useful for substrates with hydrophobic character.

A preferred embodiment encompasses the acceleration of the association rate constant for complementary nucleic acids. The following provides details of this embodiment.

IV. NUCLEIC ACID RENATURATION

A. Nucleic Acid Renaturation Using Heterogeneous Ribonucleoproteins [hnRNP]

HnRNPs are naturally occurring proteins found in ribonuclear core particles which are approximately 20 nm in diameter and have a sedimentation coefficient of about 40S. The core particles are found in a variety of eukaryotes including fruit flies, rodents and man. The core particles are comprised of both ribonucleic acid and multiple core proteins. The precise purpose of the particles or of the role of hnRNP is not presently understood. It is known that these particles are commonly associated with newly transcribed messenger RNA. It is presumed that they play a role in the splicing of the message.

The hnRNPs of use in this invention are obtained from the core proteins of the heterogeneous nucleoprotein particle. This particle is typically made up of several different core proteins ranging from 32,000 to 42,000 daltons. The core proteins of use in this invention are distinguished by their typically being the smallest protein of the group and by their carboxy termini which are capable of nucleic acid:hnRNP/nucleic acid:hnRNP intermolecular attraction. The determination of nucleic acid:hnkNP/nucleic acid:hnRNP interactions is made through routine titration experiments where acceleration of annealing is measured (see example section).

One can identify hnRNP proteins of use in this invention by passing a protein extract over a single stranded DNA column, and isolating proteins which bind to the column by elution with increasing salt concentrations. This eluate will accelerate hybridization, with A1 hnRNP protein being particularly effective. Proteins which lack significant secondary structure by circular dichroism measurements would also be expected to be particularly useful. Alternatively, one can predict in some hnRNP core proteins which will accelerate hybridization by identifying the presence of a glycine-rich (approximately 40%) COOH terminus. The determination of a glycine rich termini is made by comparing the number of glycines present in the first half of the protein with the second half. (J. Biol. Chem. 263:3307–3313, 1988).

A preferred hnRNP is a human core protein typically designated A1 hnRNP. It may be obtained as a naturally occurring protein by purification from HeLa cells or as a heterologous expression product by isolation from a genetically engineered cell expressing the A1 hnRNP gene or cDNA.

The preferred method of isolating natural-occurring hnRNP is as described in detail by Kumar et al. J. Biol. Chem. 261:11266–11273, 1986. In brief this method involves the isolation of the 20-nm monoparticles from purified nuclei. The monoparticles are isolated in a sucrose density gradient. Core protein A1 is obtained by one-step chromatographic procedure which relies on the inherent tendency of the other core proteins to aggregate into polymorphic forms. The 40S particles are dialyzed into a buffer of 2.0M NaCl to dissociate the particles. The extract is further enriched with A1 by elution through a gel filtration column in the high salt buffer with SH-reagents and collecting the appropriate fraction.

Alternatively, cDNA encoding the rat A1 hnRNP gene has been cloned and the native protein purified from mouse myeloma MOPC-21 cells according to Cobianchi, et al., J. Biol. Chem. 261:3536–3543, 1986. The Cobianchi reference also provides the nucleotide sequence for the rat A1 hnRNP.

HnRNP (about 0.5 mg/ml) is fairly stable and can be stored at −80° C. in 10 mM Tris pH 8.0, 0.1 mM EDTA, 0.1 mM dithiothreitol and 1M NaCl. Repeated freeze thawing cycles are acceptable but not recommended.

The hnRNP of use in this invention function by binding to nucleic acid and by interacting in an undefined manner to facilitate hybridization of complementary nucleic acid sequences. The carboxy terminus of these proteins are required for maximal acceleration of annealing and for intermolecular interaction (hnRNP/hnRNP interaction).

The hnRNP are substantially conserved across taxonomic genera and families. Some allelic polymorphism is found within species. In addition, through recombinant genetics, one may introduce, substitute or delete various amino acids without inhibiting the ability of hnRNP to accelerate duplex formation. For example the glycine rich domain may be enriched with equivalent amino acids such as proline. This invention and the term hnRNP is meant to embrace all proteins having the functional ability to accelerate annealing between nucleic acids. These proteins embrace both naturally occurring forms and synthetically modified forms.

B. Accelerating the rate of hybridization for nucleic acid hybridization assays

Nucleic acid hybridization assays are well known in the art. This invention is not limited to any particular mode of practicing these assays. Hybridization techniques are generally described in Nucleic Acid Hybridization a Practical Approach, Ed. Hames, B. D. and Higgins, S. J., IRL Press 1987. As improvements are made in hybridization techniques, they can readily be applied to this invention.

The acceleration of nucleic acid annealing has many uses. The uses include Northern and Southern analyses, subtractive hybridization, plaque colony screening using nucleic acid probes, and the polymerase chain reaction amplification process. Clinical applications include: diagnostic assays for pathogens, and disease states; and genetic profiling for medical or forensic uses.

Hybridization Conditions

Various hybridization solutions may be employed in the reaction mixture. Standard hybridization solutions often contain protein denaturants such as detergents, polar organic solvents such as formamide or guanidine salts. Such solutions are not recommended for protein mediated assays. The preferred solutions for this invention have a pH of between about 4.0 and about 10, most preferably between pH 6 and 8. EDTA may be included in the hybridization solutions.

Standard salt conditions for hybridization assays include the use of monovalent salts (eg. potassium or sodium) in concentrations of 1 molar or greater. Under the conditions such as provided in the examples below, high concentrations of monovalent cations have been noted as inhibiting hnRNP mediated acceleration of annealing. Although hybridization conditions may possibly be varied to obtain acceleration of annealing under high salt conditions, it is recommended that the total monovalent salt concentration be kept between about 80 and 120 mM.

The hybridization solutions may optionally contain minor amounts of magnesium salts, non-specific blocking agents, such as bovine serum albumin, unlabeled carrier nucleic acids from about 0.01 mg/ml fragmented nucleic acid, DNA, e.g., fragmented calf thymus DNA or salmon sperm DNA, or yeast tRNA or yeast RNA.

The recommended quantity of hnRNP is dependent upon the quantity of nucleic acid present in the reaction mixture. The hnRNP is thought to coat the nucleic acid with multiple hnRNP bound to each strand. For effective acceleration of annealing, a minimum of a five fold excess of hnRNP by weight over the total weight of nucleic acid present in the reaction mixture is recommended. More preferred is a 10–20 fold excess of protein by weight over the total nucleic acid. Where nucleic acid conditions are very low, increased amounts of hnRNP may be required.

Reaction temperatures will influence the hybridization rates even in the presence of hnRNP. The reaction temperature conditions are between 20°–100° C. and preferred temperatures are 37°–65° C. There is a noticeable increase in acceleration of annealing as temperatures increase with 65° C. being a preferred reaction temperature for hybridization.

Modes of Hybridization Assays

Nucleic acids hybridizations may be run in a variety of modes. It is expected that one of skill is familiar with nucleic acid hybridization assays and no attempt is made here to describe in detail the various modes available to workers in the field. The acceleration of annealing with hnRNP can be achieved in both homogeneous and heterogeneous nucleic acid hybridization assays.

Homogeneous nucleic acid hybridization assays involve assays where both complementary nucleic acids are free in solution. Heterogeneous assays involve the immobilization of at least one nucleic acid polymer to a solid support. These supports include but are not limited to filter papers, gels, nylon, magnetic beads, glass, carboxy and amino activated inert solids such as teflon or plastics. Immobilization can be noncovalent through ionic or hydrogen bonding interactions or through covalent bonding. Heterogeneous assays are well known in the art.

The reaction modes include but are not limited to binary, ternary or quaternary levels. Binary modes are reactions which rely only upon annealing between two separate nucleic acids, one of which is typically labeled. Ternary and quaternary modes involve sandwich assays where multiple nucleic acid polymers are annealed to each other.

Detection of Hybridization

The hnRNP mediated annealing does not effect the means for detection of hybridization. All standard methods are useful. These include radioisotopes, fluorophores and enzymes (eg. horseradish peroxidase or alkaline phosphatase) as reporters or labels. The reporters can be either directly attached to one of the nucleic acid polymers or indirectly attached through a ligand/receptor configuration. Methods for detection are well known in the art and variations and improvements are within the scope of this invention.

C. Other Renaturing Compounds

This invention also provides for a method of accelerating hybridization at elevated temperatures (above 45° C.). The compounds of use in this method include single stranded nucleic acid binding proteins. These proteins include hnRNP and polylysine. Such proteins are known in the art as mediators of nucleic acid annealing. (See for example J. Mol. Biol. 115:441, 1977; Proc. Natl. Acad. Sci. USA 82:5666–5670, 1985 and Biochemistry 28:1062–1069, 1989). Other compounds include cationic detergents such as hexadecyltrimethylammonium bromide and dodecyltrimethylammonium bromide.

The reaction conditions are as provided are operable for hnRNP. Optimal reaction conditions may require some routine titration experiments. Undesired results are reflected by conditions which result in nonspecific aggregate formation or unaccelerated hybridization. Such results are readily monitored by routine methods known to those of skill.

D. Kits

The invention also encompasses multi-compartmented kits using the components disclosed herein for conducting the described methods. Such kits would include the secondary bind partners either attached or unattached to a primary binding partner. Primary binding members may also be included. Means for detecting or measuring binding between primary or secondary members could also be included in these kits.

All references are incorporated by reference herein. The following examples are offered by way of illustration and not by way of limitation.

EXAMPLES

1. The Promotion of Eco R1 Restriction Enzyme Binding with its Corresponding Restriction Site Restriction enzymes are widely used tools in molecular biology. They recognize, and subsequently cleave, DNA at specific sequences. The rate with which restriction enzymes are found to associate with their corresponding binding sites can be facilitated by the addition of high probability binding partners. The Eco R1 restriction enzyme is well known. The gene encoding this enzyme is available, as are methods for modifying, overproducing and purifying the protein (see, for example *Proteins* 7:185–197, 1990). The crystal structure of Eco R1 is also known. (Science 234, 1526–1534, 1986). In this example, DNA sequence encoding a high probability binding site composed of a repeating unit of (Glycine3-Lysine1) is cloned into the gene for Eco R1 at the amino terminus. The number of repeating units is ten. The gene encoding this novel enzyme is expressed, and the protein purified. This enzyme is then used to bind to fragments of DNA containing the sequence GAATTC. These fragments are 50 and 1000 base pairs in length. Binding is measured by known techniques (*PNAS* 79:4010–4014, 1982). The monovalent cation concentration is titrated to optimize for the rate of association of the protein to the nucleic acid. Under some conditions, the rate of association is faster for the Eco R1 enzyme containing the high probability binding site. Magnesium is also included in the reaction to promote cleavage. This is an example of the third embodiment as described above.

2. The Acceleration of Nucleic Acid Hybridization Using A1 hnRNP

A comparison of nucleic acid hybridization rate in the presence of A1 hnRNP and in its absence demonstrates the dramatic hnRNP mediated increase in the rate of hybridization. The assays used nucleic acid from a Hind III/Bgl II digestion of plasmid pSV2gpt (*Science* 209:1422–1427, 1980). This double stranded segment has 120 nucleic acid bases per strand and comprises a DNA segment adjacent to the xanthine guanine phosphoribosyl-transferase gene from *E. coli*. Both strands were end labeled with $^{32}P$ by filling the recessed 3' ends according to Maniatis, T., Fritsch, E. F., and Sambrook, J., 1982, Molecular Cloning: A Laboratory Manual, Cold Spring Harbor Laboratory, Cold Spring Harbor, N.Y. [Maniatis] (at page 113). The count was approximately $10^8$ cpm per microgram of nucleic acid.

The nucleic acid was placed in a hybridization reaction mixture of 20 μl containing, 10 mM potassium phosphate pH 7.0, 1 mM EDTA, 100 mM NaCl, 1.25 ng/ml of the end-labeled complementary nucleic acid (previously rendered single stranded by heating at 95° C. for 5 minutes with 10 mM potassium phosphate buffer/1 mM EDTA and rapid chilling in ice water until added to the reaction mixture), and 711 ng/ml of A1 hnRNP (added last to the experimental mixtures). The reaction mixtures were incubated at 65° C. for 0, 1, 2, 4, 8, 16 and 32 minutes.

The reactions were stopped by diluting 5 μl of the reaction mixture to 20 μl final volume of solution containing 0.1% SDS, 50 μg/ml tRNA, 5% glycerol, and 0.05% bromphenol blue. The reaction products were then extracted with phenol:chloroform (1:1) and the aqueous phase was loaded onto a 10% polyacrylamide gel and electrophoresed for 2 hours at 10 V/cm. The gels were run in a Tris/borate buffer according to Maniatis (1982 at page 454) The gels were then dried and subjected to autoradiography to determine the extent of hybridization. The extent of hybridization was readily determined by comparing the density of single stranded DNA to double stranded DNA in each lane on the gels. Under the given conditions, there is no appreciable annealing detected after 32 minutes without A1 hnRNP. The half-time for annealing under the identical conditions with A1 hnRNP present is less than about 1 minute.

3. The Influence of A1 hnRNP on Acceleration of Nucleic Acid Hybridization Rates Compared to Standard Hybridization Conditions The reaction conditions were identical to those given in example 2 except reaction mixture A contained 120 mM potassium chloride and 400 ng/ml A1 hnRNP. Reaction mixture B contained 1M NaCl representing standard hybridization conditions. Reaction mixture A was incubated for 5 minutes at 65° C. and mixture B was run for 5 minutes at 68° C. The autoradiographic results indicated that after five minutes, reaction mixture A contained 100% duplexed nucleic acid and no detectable single stranded nucleic acid. Mixture B had no detectable double stranded nucleic acid.

The relative acceleration was estimated to be at least 100 fold faster due to A1 hnRNP.

4. The Influence of Temperature Upon the A1 hnRNP Mediated Acceleration of Nucleic Acid Hybridization Rates The reaction conditions were identical to the reaction conditions provided in example 2 except the mixtures had 4000 ng/ml A1 hnRNP. The reaction mixtures were incubated for 5 minutes at 0°, 23°, 37°, 50° and 65° C. The results demonstrated that acceleration was optimized at the higher temperatures with 100 percent of the label being associated with the double stranded nucleic acid at 65° C. after 5 minutes and about 50% of the label being found in the double stranded nucleic acid after 5 minutes at 37° C.

5. A1 hnRNP Mediated Acceleration of Nucleic Acid Hybridization in the Presence of Excess Heterologous DNA To establish that A1 hnRNP would accelerate nucleic acid hybridization in the presence of excess heterologous DNA such as would be found in a clinical sample, reactions were run in the presence of M13MP18 single stranded DNA (M13⁻) or M13MP18 single stranded DNA having the same 120 bp target sequences, as described above, cloned into it (M13⁺). The reaction conditions were identical to example 2 except the A1 hnRNP was at 16,000 ng/ml. The temperature was at 65° C. and each reaction was allowed to hybridize for 5 minutes. Reaction mixture A contained no heterologous DNA. Reaction mixture B contained a 1000 fold excess of only M13⁻ (25 ng). Reaction mixture C contained M13⁻ (22.5 ng) and M13⁺ (2.5 ng). Reaction mixture D contained only M13⁺ (25 ng). After 5 minutes at 65° C., the hybridizations were completed. No significant inhibition of hybridization was detected in mixture B over mixture A. No significant inhibition of hybridization was noted in mixtures C and D wherein it was clearly established that the placement of the target within flanking noncomplementary sequences does not inhibit the ability of A1 hnRNP to effectively accelerate the hybridization rates. Similar results were obtained with boiled genomic DNA replacing the M13MP18 DNA. No strong preference was noted for the annealing of the short nucleic acids (probes) to the target sequences regardless of whether the target was a short fragment or a part of a larger fragment (cloned into a M13 DNA). Moreover, the experimental results were analogous when the hybridizations were run at 37° C. although hybridization rates are slower.

6. The Acceleration Nucleic Acid Hybridization in Solution Using Hexadecyltrimethylammonium Bromide (CTAB)

The reaction conditions were identical to the reaction conditions provided in example 2 except that A1 protein is replaced with CTAB at a final concentration of 0.1%, and the reaction mixtures were incubated at 70° C. for 1 minute. The results demonstrate that renaturation in the presence of CTAB under these conditions allows for renaturation of strands at a rate of approximately $10^7$ (liters) (moles nucleotide$^{-1}$) (second$^{-1}$), and is more than 300 fold faster than similar reactions performed in the absence of a secondary binding partner.

7. The Acceleration of Nucleic Acid Hybridization Between Filter-bound DNA and DNA in Solution Using CTAB Two nanograms of M13+ DNA (see example 5) were spotted onto a 25 mm² Nytran® (Schliecher & Schuell, Keene, N.H.) filter and immobilized using ultraviolet radiation from a Stratagene (La Jolla, Calif.) Stratalinker (using UV doses recommended by the manufacturer). The filter was placed on top of three pieces of Whatman 3 MM paper which were pre-wetted with water and the filter was rinsed by adding water to the top of the filter, and removing solution from the underlying Whatman paper with additional dry paper. This procedure allows solution added to the top of the Nytran filter to pass through the filter. Then, fifty microliters of a solution containing 100 picograms of the 124 nt labeled, single-stranded probe DNA, 10 mM potassium phosphate (KPO₄) (pH 7.0), 1 mM EDTA, 0.4M NaCl, and 0.1% CTAB was added to the top of the filter, and the solution was allowed to pass through the filter. The filter was then subjected to four successive 10 minute incubations at 60° C. in buffers containing 10 mM KPO₄, 1 mM EDTA, and the following: 1) 0.4M NaCl, 0.1% CTAB, 2) 4.0M NaCl, 0.1% 3-[(3chloroamidopropyl)dimethylammonio]-2-hydroxy-1-propanesulfonate (CHAPS-a zwitterionic detergent), 3) 4.0M NaCl, 0.1% CHAPS, 4) 0.1M NaCl, 0.1% CHAPS. The filter was subsequently dried and subjected to autoradiography. Under these conditions, signal can be readily detected after two hours. If the M13 DNA does not contain sequence complementary to the probe, significantly less signal is detected.

Although the foregoing invention has been described in some detail by way of illustration and example for purposes of clarity of understanding, it is obvious that certain changes and modifications may be practiced within the scope of the appended claims.

What is claimed is:

1. A composition comprising complementary members of a primary binding pair covalently bound to complementary members of a secondary binding pair where the members of the secondary pair have an association rate constant which exceeds the association rate constant of the primary binding pair members and wherein complementary primary binding pair members are bound to complementary secondary binding pair members such that the binding between secondary binding pair members increases the rate of association for the primary binding pair members.

2. A composition of claim 1 where the members of the secondary binding pairs bind through ionic interactions.

3. A composition of claim 1 wherein the primary binding pair members comprise an antibody and its corresponding antigen.

4. A composition of claim 1 wherein the primary binding pair members are complementary polynucleotides.

5. A composition of claim 1 wherein the covalently bound secondary binding pair members, first members, bind to secondary binding pair members, second members, where the second members are naturally occurring domains on the primary binding pair members which bind with high specificity to the primary binding pair members having the first secondary binding pair members covalently bound thereto.

6. A composition of claim 5 wherein the primary binding pair members bound to the first members are enzymes.

7. A composition of claim 5 wherein the primary binding pair members bound to the first members are polynucleotides.

8. A composition of claim 5 wherein the primary binding pair members bound to the first members are antibodies.

9. A method for increasing the association rate constant for members of primary binding pairs in the absence of aggregate formation by the primary binding pairs; said method comprising (a) combining the primary binding pair members in an aqueous solution wherein at least one of the primary binding pair members is covalently bound to a multivalent association rate enhancer; and, (b) incubating the binding pairs under conditions which permit association of the binding pairs and the multivalent rate enhancers.

10. A method for increasing the association rate constant for members of a primary binding pair in an enzyme reaction wherein primary bind pair consists of an enzyme and substrate, said method comprising:

(a) attaching a polymer to the enzyme, said polymer binding with high probability to the substrate such that the polymer and substrate have a $k_a$ larger than the $k_a$ of the enzyme and substrate said $k_a$ being measured when the polymer and enzymes are physically apart; and (b) placing the members in an aqueous solution under conditions which permit binding between members of the primary binding pair.

11. A method of claim 10 wherein the enzyme is a nuclease.

12. A method of claim 10 wherein the enzyme is a protease.

13. A method of claim 10 wherein the polymer and substrate associate through ionic interactions.

14. A method of claim 10 wherein the polymer and substrate associate through hydrophobic interactions.

15. A method for increasing the association rate constant for members of primary binding pairs, said method comprising (a) covalently attaching complementary members of secondary binding pairs to complementary members of primary pairs where members of the secondary binding pairs have a $k_a$ larger for each other than the $k_a$ of the members of the primary binding pairs for each other and where the members of the secondary binding pairs are attached in a manner permitting them to associate with their respective complementary members thereby increasing the association rate constant for the primary binding pair members; and, (b) placing the members in an aqueous solution under conditions which permit binding between members of the primary binding pairs;

wherein said primary binding pairs are substantially apart prior to initiating step (b).

16. A method of claim 15 wherein the primary binding pairs are complementary polynucleotides.

17. A method of claim 15 wherein the primary binding pairs are antibodies and antigens.

18. A method of claim 15 wherein the secondary binding pairs associate through ionic charges.

19. A method of claim 15 wherein the secondary binding pairs associate through hydrophobic interactions.

20. A method of claim 15 wherein one of the primary binding pair members is immobilized upon a solid support.

* * * * *